United States Patent [19]

Snyder, Jr. et al.

[11] Patent Number: 5,316,686

[45] Date of Patent: May 31, 1994

[54] PERFLUOROALKYLETHER TERTIARY ALCOHOLS

[75] Inventors: Carl E. Snyder, Jr., Trotwood; Lois J. Gschwender, Kettering; Kalathil C. Eapen; Grace J. Chen, both of Fairborn, all of Ohio

[73] Assignee: The United States of America as represented by the Secretary of the Air Force, Wright-Patterson Air Force Base, Ohio

[21] Appl. No.: 3,064

[22] Filed: Jan. 11, 1993

[51] Int. Cl.$^5$ .......................................... C10M 131/10
[52] U.S. Cl. ........................................ 252/54; 252/58; 568/615; 568/677; 568/842; 568/844
[58] Field of Search .................... 252/54, 58; 568/615, 568/677, 842, 844

[56] References Cited

U.S. PATENT DOCUMENTS

| | | | |
|---|---|---|---|
| 3,293,306 | 12/1966 | Le Bleu et al. | 252/54 |
| 4,097,388 | 6/1978 | Snyder et al. | 252/49.9 |
| 4,431,845 | 2/1984 | Young et al. | 568/607 |
| 4,468,527 | 8/1984 | Patel | 568/615 |
| 5,137,650 | 8/1992 | Kaneko | 252/54 |
| 5,188,747 | 2/1993 | Kai et al. | 252/54 |

OTHER PUBLICATIONS

Graham et al., "Fluoridelon . . . " J. Org Chem 31 (1966), 957–958.

Denson et al., "Synthesis of . . . ", J. Fluorine Chem. 10 (1977), 75–80.

Sun et al., "Liquid Alkoxides . . . ", J. Fluorine Chem., 17 (1981), 457–461.

Chen et al., "Fluoro-Ketones VII . . . ", J. Fluorine Chem, 26 (1984) 341–358.

*Primary Examiner*—Jacqueline V. Howard
*Attorney, Agent, or Firm*—Charles E. Bricker; Thomas L. Kundert

[57] ABSTRACT

Perfluoroalkylether (PFAE) tertiary mono- and poly-alcohols of the general structure:

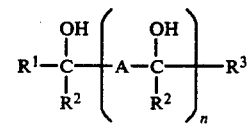

wherein $R^1$ and $R^3$ represent perfluoroalkyl groups having from one to fifty carbon atoms or PFAE groups having 2–50 carbon atoms and 1–49 oxygen atoms; $R^2$ represents a PFPAE group having 3–50 carbon atoms and 1–48 oxygen atoms; A represents perfluoroalkylene groups containing 2–30 carbon atoms or perfluoroalkyleneether groups having 2–30 carbon atoms and 1–29 oxygen atoms; and n is an integer having a value ranging from zero to ten; and wherein the alcohol contains at least 12 carbon atoms per molecule. The perfluoroalkylether (PFAE) tertiary mono- and poly-alcohols are mixed with perfluoropolyalkylether fluids in an amount ranging from 0.01 to 1.00 weight percent to provide fluids having improved antiwear properties.

5 Claims, No Drawings

PERFLUOROALKYLETHER TERTIARY ALCOHOLS

RIGHTS OF THE GOVERNMENT

The invention described herein may be manufactured and used by or for the Government of the United States for all governmental purposes without the payment of any royalty.

BACKGROUND OF THE INVENTION

This invention relates to the preparation of perfluoroalkylether (PFAE) tertiary alcohols and the chemical intermediates useful in their preparation. The invention also relates to use of such alcohols and their intermediates as antiwear additives for perfluorinated fluids.

Highly fluorinated compounds have long been of interest because of their excellent potential for high temperature applications. Fluids based on perfluoropolyalkylethers (PFPAE) have, in addition to high thermal and oxidative stability, a wide liquid range which make them ideal candidates for aerospace applications. These fluids consist essentially of a mixture of linear fluorinated polyethers. These fluids have the general formula:

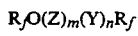

$R_fO(Z)_m(Y)_nR_f$ wherein $R_f$ is a lower perfluoroalkyl group, such as $CF_3$, $C_2F_5$, $C_3F_7$ and the like, wherein Z is $-CX_2CX_2O-$, $-CX_2CX_2CX_2O-$ or $-CX_2OCX_2CX_2O-$, where X is $-F$, $-CF_3$, $-C_2F_5$ and the like, and Y is $-CFXO-$, m and n are integers whose sum is between 2 and 200 and the ratio of n to m is between 0.1 and 10, and wherein the Z and Y units are statistically distributed along the PFPAE chain. Commercial base fluids of this type have been available for some time, for example, Krytox ® (DuPont), Fomblin ® (Montedison), Demnum ® (Daikin) and the like. Their practical utility in aerospace and military applications has been hampered by the wear and corrosion of certain metal components exposed to these base fluids under extreme conditions.

Deficiencies in base fluids are generally removed and the performance of the fluids improved by the use of additives. Conventional additives developed for the improvement of a variety of specific properties of hydrocarbon base fluids are generally not suitable for perfluorinated fluids. These conventional additives are not soluble in perfluorinated fluids and are ineffective. One way of overcoming this incompatibility is to synthesize compounds containing fluoroalkylether groups plus selected functional groups for specific activity. Although this approach may make the compound soluble in a fluorinated base fluid, mere replacement of hydrocarbon groups with fluorocarbon groups can change the useful properties of the additive itself by changing the properties of the critical functional group present in the additive. These difficulties are well known to those familiar with the art. In spite of these difficulties, a few useful additives have been developed for perfluorinated fluids. One such example is the development of PFAE substituted triphenylphosphines, C. E. Snyder, Jr. and C. Tamborski, U.S. Pat. No. 4,097,388. These additives, when dissolved in PFPAE fluids, have significantly reduced the corrosion of certain metal components exposed to the fluid at high temperatures in an oxidative environment. Reducing corrosion of the metal components exposed to a PFPAE fluid is only one of the requirements for its successful application as a functional fluid in the range of $-65°$ to $700°$ F. The problem of wear of metal components must be addressed. An antiwear additive should have sufficient solubility in the PFPAE fluid even at $-65°$ F. Another requirement is that in order to be effective for long periods of time at temperatures as high as $700°$ F., the antiwear additive should have low volatility characteristics. Such stringent property requirements are not essential when these antiwear additives are used for other applications such as instrument oils, space lubes, etc. For instance the antiwear additives for space lubes require low vapour pressure but not high temperature stability. Thus in order to incorporate the required combination of properties in the additive for different applications, it is desirable that the methods used for the synthesis of these additives readily permit structural variations in terms of the number of active functional groups per molecule as well as the nature of the pendant groups. It is additionally desirable if the starting materials necessary for the synthesis of the aforementioned antiwear additives are readily available or can be easily synthesized.

Accordingly, it is an object of this invention to provide a novel antiwear additive for perfluoropolyalkylethers.

Another object of this invention is to provide a method for making novel antiwear additives for perfluoropolyalkylethers.

A further object of this invention is to provide perfluorinated fluids improved antiwear properties Other objects and advantages of the invention will be apparent to those skilled in the art.

SUMMARY OF THE INVENTION

In accordance with the present invention, there are provided perfluoroalkylether (PFAE) tertiary mono- and poly-alcohols of the following general structure:

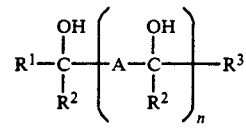

wherein $R^1$ and $R^3$ represent perfluoroalkyl groups having from one to fifty carbon atoms or PFAE groups having 2–50 carbon atoms and 1–49 oxygen atoms; $R^2$ represents a PFPAE group having 3–50 carbon atoms and 1–48 oxygen atoms; A represents perfluoroalkylene groups containing 2–30 carbon atoms or perfluoroalkyleneether groups having 2–30 carbon atoms and 1–29 oxygen atoms; and n is an integer having a value ranging from zero to ten. The groups $R^1$, $R^2$, $R^3$, and A may be branched or unbranched. It is essential that at least one of these groups contain oxygen atoms in the form of ether linkages in order for the additive to achieve solubility in PFPAE base stocks. For ease of preparation of the alcohols, it is preferable that $R^2$ have an oxygen atom attached to the second carbon from the one attached to the hydroxyl group. For application at very low temperatures the additive should have a high percentage of ether linkages to maximise solubility in the PFPAE base stock. The groups $R^1$, $R^2$ and $R^3$ may be the same or different within the specifications described above. The presence of aryl groups in these substituents would generally be less desirable in these alcohols and their intermediates, but might be tolerated if the product properties are not seriously compromised thereby. The A groups may be the same or different within the specifications described above. In order to provide the desired low volatility characteristic, the mono-/poly-alcohols of this invention should contain at least 12 carbon atoms per molecule, preferably at least 15 carbon atoms and, more preferably, at least 20 carbon atoms.

The perfluoroalkylether tertiary alcohols of this invention are prepared by first preparing a perfluoroalkyl or perfluoroalkylether ketone and reacting the resulting ketone with a perfluoroalkylether organometallic compound, as will be later shown. The present invention also includes perfluoroalkylether ketones containing at least 9 carbon atoms of the formula:

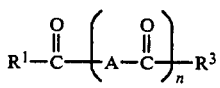

wherein A, $R^1$, $R^3$ and n are as previously described; and perfluoroalkylether ketoalcohols containing at least 15 carbon atoms of the formula:

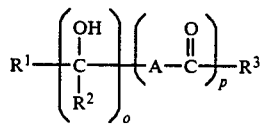

wherein A, $R^1$, $R^2$, and $R^3$ are as previously described, and o and p are integers each having a value ranging from 1 to 9, and wherein the sum of o and p is 2 to 10.

The perfluoroalkylether (PFAE) tertiary mono- and poly-alcohols are mixed with perfluoropolyalkylether fluids in an amount ranging from 0.01 to 1.00 weight percent to provide fluids having improved antiwear properties.

DETAILED DESCRIPTION OF THE INVENTION

Exmples of $R^2$ groups include $(CF_3)_2CFOCF_2CF_2-$, $C_2F_5-O-(CF_2CF_2O)_{4-5}CF_2CF_2-$,

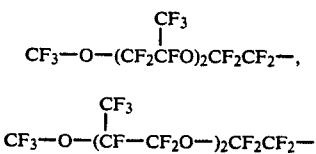

and the like. Examples of $R^1$ and $R^3$ groups include $R^2$, $(CF_3)_2CFOCF_2CF_2CF_2CF_2-$, $-nC_6F_9$, and the like. Examples of A include $-CF_2CF_2-$, $-CF_2CF_2CF_2-$, $-(CF_2)_2O(CF_2)_5O(CF_2)_2-$, $-(CF_2)_4O(CF_2)_4O(CF_2)_4-$, $-(CF_2)_2O(CF_2)_4-$, and the like.

The PFAE tertiary alcohols of this invention are prepared by preparing a perfluoroalkyl or PFAE ketone and reacting the ketone with a PFAE organometallic compound, as shown by the following reaction sequence:

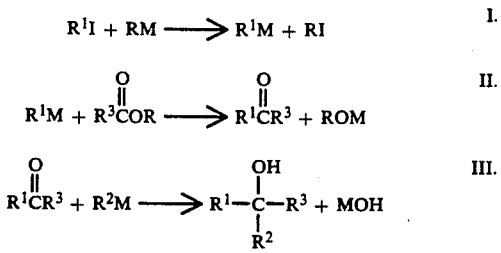

In the sequence above, R is a lower alkyl having 1 to 4 carbon atoms.

The perfluoroalkyl or PFAE ketone is prepared by the reaction of a perfluoroalkyl or PFAE iodide with an organometallic compound at a temperature ranging from $-78°$ C. to $100°$ C. in a suitable solvent or solvent mixture (Reaction I). Suitable organometallic compounds include alkyllithium compounds, alkylmagnesium halides (Grignard reagents), alkylsodium compounds, dialkylzinc compounds and the like, with the alkyllithium compounds being the most preferred at temperatures near $-78°$ C. The solvent used can be hydrocarbon ethers such as diethylether, tetrahydrofuran, glyme solvents or fluoroethers such as Freon E solvents, cyclic perfluoroethers such as FC75, perfluoro(2-butyl tetrahydrofuran) or the like as well as mixtures thereof. The preferred solvent system is diethylether, Freon E2, perfluoro(2-butyltetrahydrofuran) or mixtures thereof. The reaction requires anhydrous conditions and is carried out by the careful addition of the organometallic reagent to the iodide. The resulting perfluoroalkyl or PFAE organometallic species is not isolated, but is treated with a lower alkyl ester of a perfluoroalkyl or PFAE carboxylic acid to obtain a monoketone on hydrolysis (Reaction II).

The ketone is reacted with a PFAE organometallic compound at a temperature ranging from $-78°$ to $100°$ C., depending on the stability of the organometallic reagent used (Reaction III). The lowest possible temperature within this range is employed when a lithium intermediate is used and the highest when a zinc reagent is used. After the reaction is complete, hydrolysis with a dilute acid yields the expected alcohol. The product is purified by distillation or by chromatographic methods.

The process described above is modified to prepare polyketones. For example, reaction of a suitable diester with an organometallic compound generated from a monoiodide is utilized in obtaining a diketone:

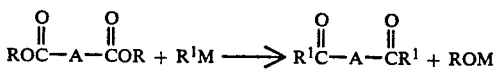

As an alternative, suitable organometallic species could also be made from diiodides and reacted with monoesters to obtain diketones:

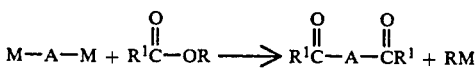

Extension of this reaction to suitable starting materials for the preparation of tri- and tetra-ketones would be obvious to the skilled worker. For example triketones may be made as follows:

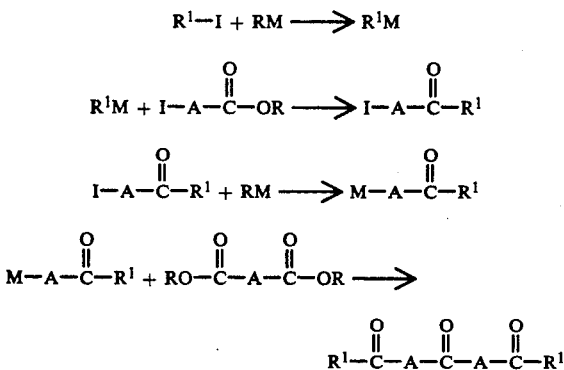

Tetra ketones may be made by either the reaction of a monoester with organometallic species from diiododiketone or by the interaction of an organometallic derivative of an iodoketone with a diester.

Particularly when the reactions described above involve a perfluoroalkyl or PFAE lithium intermediate whose stability is less than anticipated, an alternate approach has been successfully used. This involves in-situ reactions where an alkyl lithium compound such as methyl lithium in diethylether is gradually added to a mixture of perfluoroalkyl or PFAE iodide and an ester cooled to the desired low temperature. Thus a perfluoroalkyl or PFAE lithium compound is generated and immediately allowed to react with the ester to form the ketone on hydrolysis. There is a tendency for these ketones formed to undergo hydration to yield geminal diols. Therefore when required, these ketones are distilled with dehydrating agents like phosphorus pentoxide and the like to obtain anhydrous ketones and are stored in moisture-free conditions till they are used further.

Essentially similar techniques are used for the preparation of di-, tri-, and tetraalcohols. By selecting suitable organometallic species and, or solvent and, or ratio of reactants during this step, it is possible to obtain ketoalcohols from di-, tri- and tetraketones. This offers another class of intermediates in the preparation of these PFAE tertiary alcohols that are also found to be useful as antiwear additives in perfluorinated fluids.

As is obvious from the above description of our invention, a wide variation of structural features is possible in both the final products as well as intermediates used. The following examples further illustrate the invention:

EXAMPLE I

Synthesis of the monoketone

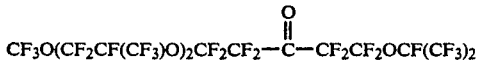

A solution of 25.8 g $(CF_3)_2CFOCF_2CF_2I$ (62.6 mmol) in 200 ml anhydrous diethylether was placed in a 500 ml three-necked round bottom flask equipped with a stirrer, thermocouple and a dropping funnel and kept under an atmosphere of dry nitrogen. The flask was cooled to $-78°$ C. in a dry-ice/isopropanol bath. While stirring the contents, 44.7 ml of 1.4M methyl lithium in diethylether was slowly added during a period of 40 minutes. After stirring the contents for an additional 30 minutes, a solution of 33.8 g of $CF_3O(CF_2CF(CF_3)O)_2CF_2CF_2COOCH_3$ (58.7 mmole) in 10 ml diethylether was added over a period of 50 minutes. After stirring the contents for a further period of 1.5 hours at $-78°$ C., the reaction mixture was hydrolyzed by the careful addition of 5 ml concentrated HCl at $-78°$ C. The contents were then poured into 100 ml of 2N HCl. The organic layer was separated, washed with water and dried over anhydrous magnesium sulfate. It was concentrated on a rotary evaporator. A GLC analysis of the product indicated that the expected ketone was present in 98% (in GLC area %). Distillation of the crude product gave 46.6 g of a colorless liquid (96% yield) boiling at 200° C. Its infrared spectrum showed an absorption at 1790 cm$^{-1}$ due to carbonyl group and its mass spectrum supported the expected structure for the ketone. Analysis for $C_{15}F_{30}O_5$. Calculated: C, 21.7%. Found: C, 21.40.

EXAMPLE II

Preparation of the monoalcohol $R^1(R^2)(R^3)COH$, wherein $R^1$ is $CF_3O(CF_2CF(CF_3)O)_2CF_2CF_2—$ and $R^2$ and $R^3$ are $(CF_3)_2CFOCF_2CF_2—$ A solution of 19.2 g of $(CF_3)_2CFOCF_2CF_2—I$ (46.6 mmol) in 250 ml anhydrous diethylether was placed in a 500 ml three-necked round bottom flask equipped with a stirrer, thermocouple and a dropping funnel and kept under an atmosphere of dry nitrogen. The flask was cooled to $-78°$ C. in a dry-ice/isopropanol bath and while stirring the contents, 33.2 ml of 1.4M methyl lithium in diethylether (46.5 mmoles) was added during 30 minutes. After stirring the contents at $-78°$ C. for another 20 minutes, a solution of the ketone (35.0 g, 42.2 mmoles) prepared in example I, and dissolved in perfluoro-(2-n-butyltetrahydrofuran) (20 ml) was added during 45 minutes. The reaction mixture was then stirred at $-78°$ C. for another 18 hours. It was hydrolyzed at $-78°$ C. with concentrated HCl (10 ml) and then poured into a mixture of 2N HCl (150 ml) and diethylether (150 ml). The organic layer was separated washed with water and dried over anhydrous magnesium sulfate. Distillation yielded 36.6 g of the pure alcohol (yield 80%). b.p. 159° C./25 mm. Its infrared spectrum showed an absorption at 3613 cm$^{-1}$ due to hydroxyl group and was free from carbonyl absorption. Its mass spectrum was consistent with the expected structure. Analysis for $C_{20}HF_{41}O_6$. Calculated: C, 21.52; H, 0.09%. Found: C, 21.32: H, 0.18%.

EXAMPLE III

Preparation of the diketone $R^1C(O)—A—C(O)R^3$ from a diester, where $R^1$ and $R^3$ are $(CF_3)_2CFOCF_2CF_2—$ and A is $—(CF_2)_3—$ A one-liter three-necked round bottom flask was dried in an oven and fitted with a stirrer, thermocouple and a dropping funnel and kept under an atmosphere of dry nitrogen. A solution of 28.0 g of $(CF_3)_2CFOCF_2CF_2—I$ (68.0 mmol) in 500 ml anhydrous diethylether was placed in the flask and the flask cooled to $-78°$ C. in a dry-ice/isopropanol bath. A solution of 48.0 ml of 1.4M methyl lithium (67.2 mmol) in diethylether was added during 20 minutes while stirring the contents. After another 20 minutes, a solution of 8.0 g of diethylhexafluoroglutarate (27.0 mmol) in diethylether (20 ml) was added during 25 minutes. After maintaining the reaction mixture at −78° C. for an additional period of 17 hours, the contents were hydrolyzed with concentrated HCl (10 ml) and then poured into 2N HCl (200 ml). The organic layer was separated, washed with water and dried over anhydrous magnesium sulfate. Distillation yielded the 17.1 g of the diketone (82% yield). b.p. 215° C. Its infrared spectrum showed carbonyl absorption at 1790 cm$^{-1}$ and the mass spectrum was consistent with the expected structure. Analysis for $C_{15}F_{28}O_4$. Calculated: C, 23.21. Found: C, 23.02%.

EXAMPLE IV

Synthesis of the diketone $R^1C(O)$—A—$C(O)R^3$ from a diiodide, where $R^1$ and $R^3$ are $CF_3O(CF_2CF(CF_3)O)_2CF_2CF_2$— and A is —$(CF_2)_2O(CF_2)_5O(CF_2)_2$—

A one-liter three-necked round-bottom flask was dried in an oven and was equipped with an addition funnel, stirrer and a thermocouple and maintained under an atmosphere of dry nitrogen. A mixture of 14.72 g I—A—I (20.0 mmol), 24.49 g $R^1C(O)OCH_3$ (42.5 mmol), 480 ml anhydrous diethylether and 120 ml $C_3F_7OCF(CF_3)CF_2OC(CF_3)H$ (Freon E2) was placed in the flask and the flask cooled to −78° C. in a dry-ice/isopropanol bath. While stirring the mixture a solution of methyl lithium in diethylether (28.6 ml of 1.4M, 40.0 mmol) was added during a period of 45 minutes. The contents were stirred for another 10 minutes before removing an aliquot sample for GLC analysis after hydrolysis with 2N.HCl. The analysis showed the presence of the following products: $R^1C(O)$—A—H (13%), $R^1C(O)CH_3$ (8%), $R^1C(O)$—A—I (6%), $R^1COOMe$ (13%) and $R^1C(O)$—A—$C(O)R^3$ (58%). Since the reaction was not complete, an additional amount of methyl lithium (5.0 ml of 1.4M, 7 mmol) was added to the reaction flask. The contents were stirred at −78° C. for another 50 minutes and then hydrolyzed by the addition of concentrated HCl (10 ml) at −78° C. The reaction mixture was then poured into a beaker containing 2N HCl (200 ml) and phase separated. The organic layer was dried over anhydrous magnesium sulfate. Analysis of the product by GLC showed the presence of $HR^1H$ (2%), $R^1C(O)$—A—H (17%), $R^1C(O)CH_3$ (10%), $R^1C(O)OCH_3$ (8%) and $R^1C(O)$—A—$C(O)R^3$ (61%), these being GLC area % without considering solvents. Distillation of the crude product on a spinning band column gave the pure diketone (19.5 g, 62% yield). b.p. 131° C./0.01 mm. Infrared spectrum (1791 cm$^{-1}$, C=O) and mass spectral data were consistent with the expected structure of the diketone. Analysis for $C_{29}F_{56}O_{10}$. Calculated: C, 22.15 ; Found: C, 22.24%.

EXAMPLE V

Synthesis of the ketoalcohol
$R^1(R^2)C(OH)$—A—$C(O)R^3$, where $R^1$, $R^2$ and $R^3$ are $(CF_3)_2CFOCF_2CF_2$— and A is —$(CF_2)_3$—

The reaction was set up as described in examples I to IV. A solution of methyl lithium in diethylether (22.0 ml of 1.4M., 30.8 mmol) was slowly added with stirring to a solution of $R^1I$ (12.73 g, 30.9 mmol) in dry diethylether (250 ml) maintained at −78° C. under a nitrogen atmosphere. The addition of methyl lithium was complete in 25 minutes. After stirring the contents for an additional 25 minutes at −78° C., a solution of a diketone prepared in example III, $R^1C(O)$—A—C-$(O)R^3$ (7.85 g, 10.1 mmol) in diethylether (5.0 ml) was added to the reaction mixture during a period of 5 minutes. After another 20 hours, the reaction mixture was hydrolyzed at −78° C. with concentrated HCl (5.0 ml). This was added to 2N HCl (100 ml) and phase separated. The organic layer was dried over anhydrous magnesium sulfate and the solvent removed. A GLC/MS analysis of the crude product showed the presence of the expected ketoalcohol. There was no evidence for the formation of a dialcohol under these conditions. The crude product was distilled to obtain $R^1(R^2)C(OH)$—A—$C(O)R^3$ (8.31g, 77% yield). B.P. 77°-8° C./0.01 mm). Infrared spectrum of the compound showed absorptions at 3608 cm$^{-1}$ (OH) as well as at 1790 cm$^{-1}$ (C=O). Analysis for $C_{20}HF_{39}O_5$. Calculated: C, 22.62; H, 0.09. Found: C, 22.19; H, 0.19%.

EXAMPLE VI

Preparation of the ditertiary alcohol
$R^1(R^2)C(OH)$—A—$C(OH)(R^2)R^3$, where $R^1$ and $R^3$ are $CF_3O(CF_2CF(CF_3)O)_2CF_2CF_2$—, $R^2$ is —$(CF_3)_2CFOCF_2CF_2$— and A is —$(CF_2)_2O(CF_2)_5O(CF_2)_2$—

The reaction was set up as described in earlier examples. A solution of $R^2I$ (3.30 g, 8.00 mmol) in perfluoro(2-n-butyltetrahydrofuran) (30 ml) was cooled to −78° C. and methyl lithium in diethylether (5.6 ml of 1.4M, 7.8 mmol) was added with stirring during 15 minutes. After stirring the contents for an additional 15 minutes, the diketone prepared in example IV, $R^1C(O)$—A—$C(O)R^3$ (3.15 g, 2.0 mmol) in perfluoro(2-n-butyltetrahydrofuran)(5.0 ml) was added during 15 minutes. After stirring the reaction mixture at −78° C. for another 2 hours, it was hydrolyzed by the addition of concentrated HCl (2.0 ml) followed by treatment with 2N HCl (10 ml). The organic layer was separated, washed with water (10 ml) and dried over anhydrous magnesium sulfate. GLC/MS analysis of the mixture indicated that it was the expected dialcohol contaminated with about 2% (GLC area %) of the ketoalcohol. Distillation yielded the dialcohol (4.1 g, 96% yield). It boils at 171° C. at 0.03 mm. Infrared spectrum of the pure dialcohol did not show any carbonyl absorption, but showed absorption at 3614 cm$^{-1}$ due to OH group. Analysis for $C_{39}H_2F_{78}O_{12}$. Calculated: C, 21.85; H, 0.09. Found: C, 22.08; H, 0.10.

EXAMPLE VII

Formulation and Testing

The monoperfluoroalcohol prepared in Example II, hereinafter referred to as PFA, was formulated with a linear perfluoropolyalkylether (PFPAE) having an average carbon:oxygen ratio of 1.4. A distillation cut of the PFPAE had the following viscosity temperature properties:

TABLE I

| Temperature, °C. | Kinematic viscosity, cSt |
|---|---|
| −54 | 118.0 |
| 38 | 18.08 |
| 99 | 5.75 |

Four Ball Wear Test (ASTM D-4172). Test conditions were: Balls, 52100 Bearing Steel; Speed, 600 rpm; Load, 40 kg; Temperature, 75° C.; Time, 1 hour. The composition of PFA in the PFPAE and wear scar test results are given in Table II:

TABLE II

| Test No. | Composition (wt %) PFPAE | PFA | Wear Scar (mm) |
|---|---|---|---|
| 1 | 100.00 | 0.00 | 1.03 |
| 2 | 99.95 | 0.05 | 0.98 |
| 3 | 99.90 | 0.10 | 0.60 |
| 4 | 99.85 | 0.15 | 0.64 |

Traction Test. The traction tester has independently driven, counter-rotating, crowned cylindrical discs. The device has a computerized data acquisition and control system. Test parameters are entered from the terminal. Once the test is started, the computer assumes full control of the device: it sets the motor speeds to the desired slip/roll condition, sets the load and brings the system to an equilibrium. When all the parameters are at equilibrium for 5 seconds, data is written to a computer diskette. The control system then changes the conditions for the next slip/roll, keeping other parameters the same. Data for positive and negative slips are collected for each traction curve. In case the system does not maintain equilibrium for 5 seconds, data can still be recorded by bypassing this condition. Whenever this instability occurred, the disc specimens were found to be scored in the contact region.

Traction tests were performed on unmodified PFPAE (Fluid 1) and on the composition containing 0.10 wt % PFA, balance PFPAE (Fluid 3). Disc specimens for these tests were fabricated to the following specifications: Material, 52100 bearing steel, Rc 60-63; Diameter, 3.81 cm; Crown Radii, 16.03 and 15.60 cm for the unmodified PFPAE, 15.00 and 15.49 cm for the modified PFPAE; Aspect Ratio of Elliptical Contact, Fluid 1—4.02, Fluid 3—3.92; Surface Roughness, 0.05 μm cla.

Traction data for both fluids was almost identical under the following conditions (temperature, differential speed, applied load): 85° C., 3.80 m/s, 1027 MPa; 85° C., 4.18 m/s, 1410 MPa; 141°°C., 9.49 m/s, 1410 MPa; 141° C., 17.32 m/s, 1410 MPa. Midway during the testing on Fluid 1, the system would not equilibrate for the required 5 second interval, indicating that the disc specimens were scored. Data were collected by bypassing this condition. At the completion of the test, both disc specimens were found to be badly scored. The discs were polished to the original surface roughness and the test was repeated. The discs were scored again. Further, the discs had corrosion spots outside the contact area.

Tests on Fluid 3 were completed without any scoring of the disc specimens. These discs had no corrosion spots. Data were collected in a completely automated mode without bypassing the equilibrium conditions. This demonstrates the effectiveness of the additive of this invention under elastohydrodynamic conditions.

Various modifications may be made to the invention as described without departing from the spirit of the invention or the scope of the appended claims.

We claim:

1. Perfluoroalkylether tertiary alcohols of the formula:

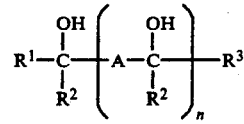

wherein $R^1$ and $R^3$ are perfluoroalkyl groups having from one to fifty carbon atoms or perfluoroalkylether groups having 2-50 carbon atoms and 1-49 oxygen atoms; $R^2$ is a perfluoroalkylether group having 3-50 carbon atoms and 1-48 oxygen atoms; A is a perfluoroalkylene group containing 2-30 carbon atoms or perfluoroalkyleneether groups having 2-30 carbon atoms and 1-29 oxygen atoms; and n is an integer having a value ranging from zero to ten; and wherein said alcohol contains at least 12 carbon atoms per molecule.

2. The tertiary alcohol of claim 1 wherein n is zero, $R^1$ is $CF_3O(CF_2CF(CF_3)O)_2CF_2CF_2-$, and $R^2$ and $R^3$ are $(CF_3)_2CFOCF_2CF_2-$.

3. The tertiary alcohol of claim 1 wherein n is 1, $R^1$ and $R^3$ are $CF_3O(CF_2CF(CF_3)O)_2CF_2CF_2-$, is $(CF_3)_2CFOCF_2CF_2-$, and A is $-(CF_2)_2O(CF_2)_5O(CF_2)_2-$.

4. A lubricating composition consisting essentially of a linear perfluorinated polyether and about 0.01 to 1.00 weight percent of at least one perfluoroalkylether tertiary alcohol of the formula:

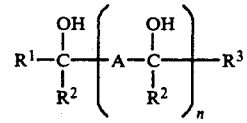

wherein $R^1$ and $R^3$ are perfluoroalkyl groups having from one to fifty carbon atoms or perfluoroalkylether groups having 2-50 carbon atoms and 1-49 oxygen atoms; $R^2$ is a perfluoroalkylether group having 3-50 carbon atoms and 1-48 oxygen atoms; A is a perfluoroalkylene group containing 2-30 carbon atoms or perfluoroalkyleneether groups having 2-30 carbon atoms and 1-29 oxygen atoms; and n is an integer having a value ranging from zero to ten; and wherein said alcohol contains at least 12 carbon atoms.

5. The composition of claim 4 consisting essentially of about 0.05 to 0.15 weight percent of said tertiary alcohol, balance said linear perfluorinated polyether.

* * * * *